(12) United States Patent
Suzuki et al.

(10) Patent No.: US 7,326,559 B2
(45) Date of Patent: Feb. 5, 2008

(54) PROCESS FOR PREPARATION OF OPTICALLY ACTIVE ALLENES

(75) Inventors: Keisuke Suzuki, Yokohama (JP); Takashi Matsumoto, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 428 days.

(21) Appl. No.: 10/506,573

(22) PCT Filed: Sep. 6, 2002

(86) PCT No.: PCT/JP02/09085

§ 371 (c)(1),
(2), (4) Date: Sep. 3, 2004

(87) PCT Pub. No.: WO03/074717

PCT Pub. Date: Sep. 12, 2003

(65) Prior Publication Data

US 2005/0106692 A1 May 19, 2005

(30) Foreign Application Priority Data

Mar. 6, 2002 (JP) ............................. 2002-061014

(51) Int. Cl.
*C12P 41/00* (2006.01)
(52) U.S. Cl. ...................................... 435/280
(58) Field of Classification Search .................. None
See application file for complete search history.

(56) References Cited

OTHER PUBLICATIONS

Landgrand et al., "Lipase Catalyzed Reactions and Strategy for Alcohol Resolution", Tetrahedron Letters 27 (1) : 29-32 (1986).*
Wang et al., Lipase-Catalyzed Irreversible Transesterificaions Using Eno Esters as Acylating Reagents: Preparative Enantio- and Regioselective Syntheses of Alcohols, Glycerol Derivatives, Sugars, and Organometallics: J. Am. Chem. Soc. 110 : 7200-7205 (1988).*
Claude Spino, "Synthesis of Non- Racemic Unsymmetrical Tetrasubstituted Vinylallens," Tetrahedron Letters, vol. 41, No. 42, 2000, pp. 8033-8036.
Giuseppe Guanti, "Chemoenzymatic Preparation of Asymmetrized Tris (Hydroxymethyl)Methane(THYM*) and of Asymmetrized Bis (Hydroxymethyl) Acetaldehyde (BHYMA*) As New Highly Versatile Chiral Building Blocks," J. Org. Chem., vol. 57, No. 5, 1992, pp. 1540-1554.
Hajime Mori, "Novel Diastereoselective Allene Formation By an Ene Reaction of Significantly Twisted 1,3-Dienes with Singlet Oxygen," Tetrahedron Letters, vol. 40, No. 35, 1999, pp. 6461-6464.

* cited by examiner

*Primary Examiner*—Sandra E. Saucier
(74) *Attorney, Agent, or Firm*—Foley & Lardner LLP

(57) ABSTRACT

The present invention provides a process for producing an optically active allene represented by formula (1):

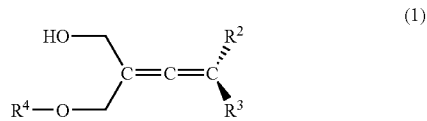

wherein $R^2$ and $R^3$ are different and each represents a hydrogen atom, an optionally substituted $C_{1-20}$ alkyl group or an optionally substituted $C_{6-20}$ aryl group, and $R^4$ represents an acyl group, which comprises reacting an allene derivative represented by formula (2):

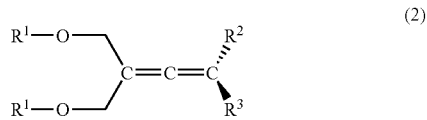

wherein $R^1$ represents a hydrogen atom or an optionally substituted acyl group and $R^2$ and $R^3$ have the same meaning as defined above, with an acylating agent having an acyl group represented by $R^4$ when both $R^1$s are each a hydrogen atom or with water when both $R^1$s are each an acyl group represented by $R^4$, in the presence of an enzyme catalyst. According to this production process, an optically active allene can be produced efficiently and enantioselectively from an allene derivative having a symmetrical structure.

10 Claims, No Drawings

PROCESS FOR PREPARATION OF OPTICALLY ACTIVE ALLENES

TECHNICAL FIELD

The present invention relates to a process for producing an optically active axially dissymmetric allene and in particular to a process for producing an optically active allene by rendering an allene derivative having a symmetrical structure asymmetrical enantioselectively by utilizing an enzyme catalyst.

BACKGROUND ART

When a certain compound can occur as a plurality of optical isomers, a certain optical isomer may exhibit a higher activity for example as a medicine or an agrochemical than that of the other optical isomers. Accordingly, asymmetric synthesis of a specific optical isomer is important particularly in the fields of medicine and agrochemical. Further, an optically active allene having axial dissymmetry is useful as a synthetic intermediate of various optically active compounds.

Conventionally, methods for optical resolution of racemic allenes by an enzyme catalyst such as lipase are known (see, for example, G. Gil et al., "Lipase-Catalyzed Ester Formation in Organic Solvents. Partial Resolution of Primary Allenic Alcohols", Tetrahedron Letters, Vol. 28, No. 15, pp. 1647-1648, 1987).

However, some methods for optical resolution of racemic allenes are known, enantioselective synthesis of allene compounds having various substituent groups is not known.

Accordingly, there has been demand for a method of synthesizing various axially dissymmetric allenes easily with high optical purity.

DISCLOSURE OF INVENTION

The present inventors focused their attention on the axial dissymmetry-recognizing ability of an enzyme applied exclusively to kinetic resolution of racemic allenes, and found that various axial dissymmetric allenes can be easily obtained with high optical purity by applying the enzyme to asymmetric synthesis of allenes by rendering allene derivatives having a symmetric structure asymmetrical, and the present invention was thereby completed.

That is, the present invention provides a process for producing an optically active allene represented by formula (1):

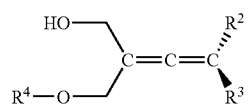
(1)

wherein $R^2$ and $R^3$ are different and each represents a hydrogen atom, an optionally substituted $C_{1-20}$ alkyl group or an optionally substituted $C_{6-20}$ aryl group, and $R^4$ represents an acyl group, which comprises reacting an allene derivative represented by formula (2):

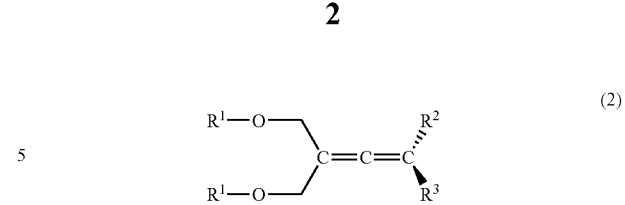
(2)

wherein $R^1$ represents a hydrogen atom or an optionally substituted acyl group and $R^2$ and $R^3$ have the same meaning as defined above, with an acylating agent having an acyl group represented by $R^4$ when both $R^1$s are each a hydrogen atom or with water when both $R^1$s are each an acyl group represented by $R^4$, in the presence of an enzyme catalyst.

BEST MODE FOR CARRYING OUT THE INVENTION

According to a preferable mode of the invention, the enzyme catalyst is a lipase enzyme or esterase enzyme. As the enzyme catalyst, use is made of at least one member selected from the group consisting of *Candida Antarctica* lipase, *Pseudomonas fluorescens* lipase, *Pseudomonas cepacia* lipase, *porcine pancreatic* lipase, *porcine liver* esterase and *Candida rugosa* lipase.

The preferably acylating agent used in the present invention includes, but is not limited to, a compound represented by the following formula (3a) or (3b):

(3a)

(3b)

wherein $R^4$ represents an acyl group.

In the formula, $R^4$ is preferably an acetyl group, a butyryl group or a benzoyl group.

In the present invention, $R^1$ is a hydrogen atom or an acyl group, preferably a hydrogen atom, an optionally substituted $C_{1-20}$ alkylcarbonyl group or an optionally substituted $C_{6-20}$ arylcarbonyl group, specifically a hydrogen atom, an optionally substituted $C_{1-10}$ alkylcarbonyl group or an optionally substituted $C_{6-10}$ arylcarbonyl group, more specifically a hydrogen atom or an optionally substituted $C_{1-4}$ alkylcarbonyl group, most specifically a hydrogen atom.

$R^2$ and $R^3$ are different from each other and are each a hydrogen atom, an optionally substituted $C_{1-20}$ alkyl group or an optionally substituted $C_{6-20}$ aryl group, specifically a hydrogen atom, an optionally substituted $C_{1-10}$ alkyl group or an optionally substituted $C_{6-10}$ aryl group, more specifically a hydrogen atom, an optionally substituted $C_{1-4}$ alkyl group or an optionally substituted $C_{6-8}$ aryl group, most specifically a hydrogen atom, methyl group, ethyl group, propyl group, butyl group, phenyl group, tolyl group or benzyloxymethoxymethyl group.

Specific $R^2/R^3$ combinations include, for example, a hydrogen atom/optionally substituted $C_{1-10}$ alkyl group, a hydrogen atom/optionally substituted phenyl group, a $C_{1-3}$ alkyl group/optionally substituted phenyl group, etc.

In this specification, the "alkyl group" is an alkyl group which may be linear or branched, and examples thereof include a methyl group, ethyl group, propyl group, n-butyl group, t-butyl group, pentyl group, hexyl group etc.

The "aryl group" includes, for example, a phenyl group, a naphthyl group such as 1-naphthyl group or 2-naphthyl group, an indenyl group such as 2-indenyl group, an anthryl group such as 2-anthryl group, a tolyl group such as 2-tolyl group, 3-tolyl group or 4-tolyl group, and a biphenyl group. The "arylcarbonyl group" includes, for example, a benzoyl group, 1-naphthoyl group, 2-naphthoyl group etc.

The "acyl group" includes a formyl group, a carboxy group, a carbamoyl group, an optionally substituted $C_{1-6}$ alkylcarbonyl group, a $C_{1-6}$ alkoxycarbonyl group (for example., a methoxycarbonyl group, ethoxycarbonyl group, propoxycarbonyl group, tert-butoxycarbonyl group etc.), an optionally substituted $C_{6-10}$ arylcarbonyl group, an optionally substituted $C_{6-10}$ aryloxycarbonyl group, an optionally substituted $C_{7-16}$ aralkyloxycarbonyl group, an optionally substituted 5- to 6-memberred heterocyclic carbonyl group, a mono-$C_{1-6}$ alkyl-carbamoyl group, a di-$C_{1-6}$ alkyl-carbamoyl group (for example, a dimethylcarbamoyl group, diethylcarbamoyl group, ethylmethylcarbamoyl group etc.) etc. The acyl group preferably used in the present invention is an acetyl group, butyryl group or benzoyl group.

The group with which the alkyl or aryl group can be substituted includes, for example, a halogen atom (for example, fluorine, chlorine, bromine, iodine etc.), a nitro group, a cyano group, an optionally halogenated $C_{1-6}$ alkyl group, an optionally halogenated $C_{3-6}$ cycloalkyl group, an optionally halogenated $C_{1-6}$ alkoxy group, an optionally halogenated $C_{1-6}$ alkylthio group, a hydroxy group, an amino group, a mono-$C_{1-6}$ alkylamino group (for example, a methylamino group, ethylamino group, propylamino group, isopropylamino group, butylamino group etc.), a di-$C_{1-6}$ alkylamino group (for example, a dimethylamino group, diethylamino group, dipropylamino group, dibutylamino group, ethylmethylamino group etc.), a formyl group, a carboxy group, a carbamoyl group, an optionally halogenated $C_{1-6}$ alkylcarbonyl group, a $C_{1-6}$ alkoxycarbonyl group (for example, a methoxycarbonyl group, ethoxycarbonyl group, propoxycarbonyl group, tert-butoxycarbonyl group etc.), a mono-$C_{1-6}$ alkylcarbamoyl group (for example, a methylcarbamoyl group, ethylcarbamoyl group etc.), a di-$C_{1-6}$ alkylcarbamoyl group (for example, a dimethylcarbamoyl group, diethylcarbamoyl group, ethylmethylcarbamoyl group etc.), an optionally halogenated $C_{1-6}$ alkylsulfonyl group, a formylamino group, an optionally halogenated $C_{1-6}$ alkylcarboxamide group, a $C_{1-6}$ alkoxycarboxamide group (for example, a methoxycarboxamide group, ethoxycarboxamide group, propoxycarboxamide group, butoxycarboxamide group etc.), a $C_{1-6}$ alkylsulfonylamino group (for example, a methylsulfonylamino group, ethylsulfonylamino group etc.), a $C_{1-6}$ alkylcarbonyloxy group (for example, an acetoxy group, propanoyloxy group etc.), a $C_{1-6}$ alkoxycarbonyloxy group (for example, a methoxycarbonyloxy group, ethoxycarbonyloxy group, propoxycarbonyloxy group, butoxycarbonyloxy group etc.), a mono-$C_{1-6}$ alkyl-carbamoyloxy group (for example, a methylcarbamoyloxy group, ethylcarbamoyloxy group etc.), a di-$C_{1-6}$ alkyl-carbamoyloxy group (for example, a dimethylcarbamoyloxy group, diethylcarbamoyloxy group etc.), a benzyloxy-$C_{1-3}$ alkoxy group etc. The number of these groups with which the alkyl or aryl group is substituted is not particularly limited, and the number of these substituent groups is for example 1 to 5, specifically 1 to 3.

Hereinafter, the production process of the present invention is described in more detail.

The optically active allene compound of the present invention can be produced for example according to the following scheme (I) when the compound of formula (2) wherein both $R^1$s are each a hydrogen atom is used as the starting material.

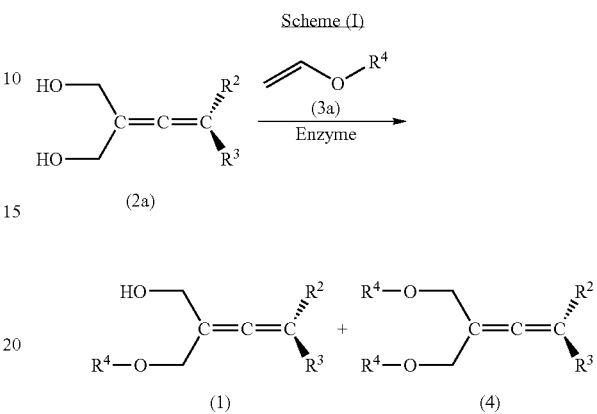

wherein $R^1$, $R^2$, $R^3$ and $R^4$ have the same meanings as defined above.

In the scheme (I) above, the allene compound represented by formula (2a) is reacted with the acylating agent represented by formula (3a) (wherein $R^4$ is for example an acetyl group, a butyryl group or a benzoyl group) in the presence of an enzyme catalyst, to give the objective compound, that is, the optically active allene compound represented by formula (1). According to a preferable mode of the present invention, the thus obtained optically active allene compound represented by formula (1) can be obtained with high optical purity. However, the compound represented by formula (4) may be formed as a byproduct depending on the type of the enzyme catalyst used, the type of the acylating agent used, and the reaction conditions. The byproduct represented by formula (4) can be separated and removed by known separation and purification meand such as various kinds of chromatographic techniques. Accordingly to the synthesis method of the present invention, an optically active allene compound having high optical purity can be synthesized. For example, an optically active allene compound having an optical purity of 70% or more, more preferably 80% or more, still more preferably 90% or more, can be obtained accordingly to the preferable mode of the present invention.

The reaction can be carried out in the presence or absence of a solvent. When the reaction is carried out in the presence of a catalyst, a solvent inert to the reaction is usually used. The solvent preferably used in the present invention includes, for example, an alcohol type solvent, an ether type solvent, a halogenated hydrocarbon type solvent, an aromatic solvent, a nitrile type solvent, an amide type solvent, a ketone type solvent and a sulfoxide type solvent. These solvents may be used as a mixture of two or more thereof in a suitable ratio. Among these solvents, a halogenated hydrocarbon type solvent such as dichloromethane and chloroform, an ether type solvent such as diisopropyl ether and tetrahydrofuran, and an aromatic solvent such as toluene are preferable.

As the enzyme catalyst used in the reaction, use is made of for example at least one member selected from the group consisting of *Candida Antarctica* lipase (CAL), *Pseudomonas fluorescens* lipase (PFL), *Pseudomonas cepacia* lipase (PCL), *porcine pancreatic* lipase (PPL), *porcine liver* esterase (PLE) and *Candida rugosa* lipase (CRL). Enzyme catalysts particularly preferably used among these are *Candida Antarctica* lipase, *Pseudomonas fluorescens* lipase and *Pseudomonas cepacia* lipase.

This reaction is carried out under reaction conditions suitably selected depending on the type of the enzyme catalyst used, etc.; for example, the reaction is conducted at a temperature of 5° C. to 40° C., preferably 20° C. to 40° C., for 10 minutes to 14 days, preferably 10 minutes to 10 days, more preferably 1 hour to 6 days, still more preferably 2 hours to 10 hours. This reaction is carried out usually under normal pressures, but can be carried out if necessary under reduced pressure or under pressure in such a range that the catalytic performance of the enzyme is not influenced.

When the compound of formula (2) wherein both $R^1$s are each an acyl group is used as the starting material, the compound of formula (2) can be subjected to reaction (hydrolysis) with water in the presence of the enzyme catalyst to give the optically active allene compound of formula (1). This hydrolysis is carried out under reaction conditions suitably selected depending on the type of the enzyme catalyst used, etc.; for example, the hydrolysis is conducted at a temperature of 5° C. to 40° C., preferably 20° C. to 40° C., for 10 minutes to 14 days, preferably 10 minutes to 10 days, more preferably 1 hour to 6 days, still more preferably 2 hours to 10 hours. This reaction is carried out usually under general pressures, but can be carried out if necessary under reduced pressure or under pressure in such a range that the catalytic performance of the enzyme is not influenced.

The optically active allene compound thus obtained can be used as an intermediate for producing active compounds such as medicines and agrochemicals.

EXAMPLES

Hereinafter, the present invention is described in more detail by reference to the Examples. However, the present invention is not limited to the Examples.

Example 1

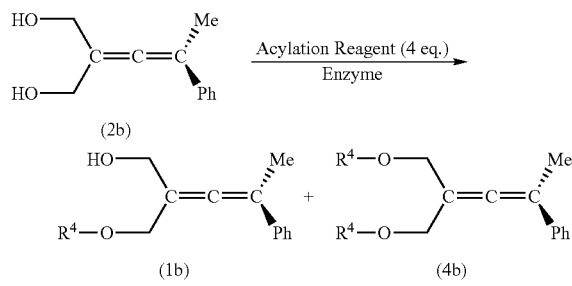

In the reaction shown above, acetoxy ethylene (0.1 mL) as acylating agent A and 25 mg *Pseudomonas fluorescens* lipase as the enzyme catalyst were added to 2-hydroxymethyl-4-phenylpenta-2,3-dien-1-ol (50.0 mg, 0.263 mmol), and the mixture was reacted in diisopropyl ether. The reaction was carried out at a temperature of 30° C. for 1.8 hours under stirring.

Thereafter, the reaction solution was diluted with ethyl acetate and then filtered to remove insolubles. The filtrate was transferred to a separatory funnel, then washed with an aqueous saturated sodium bicarbonate solution and saturated saline in this order, and dried over sodium sulfate anhydride. A crude product obtained by distilling the solvent away was purified by silica gel preparative thin-layer chromatography (developing solution: hexane/ethyl acetate=6/4) to give compounds of formulae (1b) and (4b). As a result, the compound of formula (1b) i.e. the objective optically active allene compound could be obtained in 93% yield (optical purity 90% ee) ($R^4$=Ac). In the reaction mixture, the amounts of the byproduct of formula (4b) and the compound represented by formula (2b) were as very low as about 4% respectively. Measurement results of the physicochemical properties of the resulting compounds are as follows:

Compound of Formula (2b) (2-hydroxyinethyl-4-phenyl-penta-2,3-dien-1-ol)

$^1$H-NMR (CDCl$_3$) δ 2.14 (s, 3H), 2.36 (brs, 2H), 4.33 (s, 4H), 7.19-7.41 (m, 5H)

Elementary analysis (for $C_{12}H_{14}O_2$)

Theoretical: C, 75.76; H, 7.42

Found: C, 75.47; H, 7.42

Compound of Formula (1b) (2-hydroxymethyl-4-phenyl-penta-2,3-dien-1-yl acetate)

$^1$H-NMR (CDCl$_3$) δ 2.07 (s, 3H), 2.13 (s, 3H), 2.30 (brs, 1H), 4.23 (s, 2H), 4.76 (s, 2H), 7.20-7.40 (m, 5H)

Elementary analysis (for $C_{14}H_{16}O_3$)

Theoretical: C, 72.39; H, 6.94

Found: C, 72.43; H, 7.14

Compound of Formula (4b)

$^1$H-NMR (CDCl$_3$) δ 2.06 (s, 6H), 2.12 (s, 3H), 4.70 (s, 4H), 7.24-7.39 (m, 5H)

Examples 2 to 19

Optically active allene compounds were synthesized in the same manner as in Example 1 except that the type of the enzyme and the type of the solvent were changed (or the solvent was not used).

The experimental conditions and the results are shown in Table 1.

TABLE 1

| Example | Enzyme | Solvent | Acylating agent | Time | Yield (% ee) 2b | 1b | 4b |
|---|---|---|---|---|---|---|---|
| 1 | PFL | Pr$_2$O | A | 1.8 hours | trace | 93(90) | 4 |
| 2 | CAL | none | A | 15 minutes | trace | 38(90) | 60 |
| 3 | PCL | none | A | 1.6 days | trace | 91(72) | 8 |
| 4 | PFL | none | A | 1.6 days | 0 | 50(94) | 50 |
| 5 | PFL | none | A | 5.2 hours | 6 | 92(80) | 2 |
| 6 | PPL | none | A | 3.8 days | 3 | 85(86) | 9 |
| 7 | CRL | none | A | 4.9 days | 23 | 67(46) | 10 |
| 8 | CAL | Pr$_2$O | A | 1.0 hours | 30 | 50(58) | 20 |
| 9 | PCL | Pr$_2$O | A | 1.1 days | trace | 95(88) | 4 |
| 10 | PPL | Pr$_2$O | A | 5.8 days | 47 | 49(82) | 9 |
| 11 | CAL | CHCl$_3$ | A | 20 days | 10 | 73(76) | 12 |
| 12 | PFL | CHCl$_3$ | A | >7 days | 39 | 55(78) | trace |

Examples 13 to 30

Optically active allene compounds were synthesized in essentially the same manner as in Example 1 except that the enzyme catalyst and the acylating agent were changed in order to select an acylating agent suitable for the specific enzyme catalyst. B indicates AcO—C(CH$_3$)=CH$_2$, C indicates BzO—CH$_2$=CH$_2$, D indicates Pr—C(=O)—O—

$CH_2$=$CH_2$, Ac indicates an acetyl group, Bz indicates a benzoyl group, and Pr indicates a propyl group.

The experimental conditions and the results are shown in Table 2.

TABLE 2

| Example | Enzyme | Solvent | Acylating agent | Time | Yield (% ee) 2b | Yield (% ee) 1b | Yield (% ee) 4b |
|---|---|---|---|---|---|---|---|
| 13 | PFL | none | A | 5.2 hours | 6 | 92(89) | 2 |
| 14 | PFL | none | B | >7 days | 63 | 37(—) | trace |
| 15 | PFL | none | D | 2.6 hours | 4 | 88(96) | 5 |
| 16 | PCL | none | A | 1.6 days | trace | 91(72) | 8 |
| 17 | PCL | none | B | >7 days | 69 | 31(—) | 0 |
| 18 | PCL | none | D | 5.7 hours | 6 | 90(—) | 4 |
| 19 | PPL | none | A | 3.8 days | 3 | 85(86) | 9 |
| 20 | PPL | none | B | >7 days | 90 | 10(—) | 0 |
| 21 | PPL | none | D | 18 hours | 5 | 92(—) | 2 |
| 22 | PFL | $Pr_2O$ | A | 3.0 hours | trace | 97(92) | 5 |
| 23 | PFL | $Pr_2O$ | B | 13 hours | 9 | 89(92) | trace |
| 24 | PFL | $Pr_2O$ | C | 3.3 days | 8 | 87(92) | 0 |
| 25 | PFL | $Pr_2O$ | D | 3.0 hours | 4 | 84(92) | 6 |
| 26 | PCL | $Pr_2O$ | A | 1.1 days | trace | 95(89) | 4 |
| 27 | PCL | $Pr_2O$ | B | 3.6 days | 4 | 94(—) | trace |
| 28 | PCL | $Pr_2O$ | C | >7 days | 38 | 59(86) | 0 |
| 29 | PCL | $Pr_2O$ | D | 7.0 hours | 3 | 94(86) | 3 |

As is evident from the results shown in Tables 1 to 2, the objective optically active allene compounds can be obtained in high yield according to the production process of the present invention.

INDUSTRIAL APPLICABILITY

According to the process for producing an optically active allene according to the present invention, an optically active allene can be produced efficiently and enantioselectively from an allene derivative having a symmetric structure. The optically active allene thus obtained can be preferably used as an intermediate for producing active compounds such as medicines and agrochemicals.

The invention claimed is:

1. A process for producing an optically active allene represented by formula (1):

$$\text{HO—} \diagdown \underset{R^4—O—\diagup}{C}=C=C\underset{R^3}{\overset{R^2}{\diagup}} \quad (1)$$

wherein $R^2$ and $R^3$ are different and each represents a hydrogen atom, an optionally substituted $C_{1-20}$ alkyl group or an optionally substituted $C_{6-20}$ aryl group, and $R^4$ represents an acyl group, which comprises reacting an allene derivative represented by formula (2):

$$\text{R}^1\text{—O—} \diagdown \underset{R^1—O—\diagup}{C}=C=C\underset{R^3}{\overset{R^2}{\diagup}} \quad (2)$$

wherein $R^1$ represents a hydrogen atom and $R^2$ and $R^3$ have the same meaning as defined above, with an acylating agent having an acyl group represented by $R^4$, in the presence of a lipase enzyme which is at least one member selected from the group consisting of *Candida antarctica* lipase, *Pseudomonas fluorescens* lipase, *Pseudomonas cepacia* lipase, *Porcine liver esterase* and *Candida rugosa* lipase.

2. The process for producing an optically active allene according to claim 1, wherein the lipase enzyme is at least one member selected from the group consisting of *Candida antarctica* lipase, *Pseudomonas fluorescens* lipase and *Pseudomonas cepacia* lipase.

3. The process for producing an optically active allene according to claim 1, wherein the acylating agent is a compound represented by:

$$\diagup\!\!\!\diagdown_{O}\diagdown_{R^4} \quad \text{or} \quad (3a)$$

$$\diagup\!\!\!\diagdown_{O}\diagdown_{R^4} \quad (3b)$$

wherein $R^4$ represents an acyl group.

4. The process for producing an optically active allene according to claim 1, wherein $R^1$ is a hydrogen atom, an optionally substituted $C_{1-20}$ alkylcarbonyl group or an optionally substituted $C_{6-20}$ arylcarbonyl group.

5. The process for producing an optically active allene according to claim 1, wherein $R^2$ and $R^3$ are different and each represents a hydrogen atom, an optionally substituted $C_{1-10}$ alkyl group or an optionally substituted $C_{6-10}$ aryl group.

6. The process for producing an optically active allene according to claim 1, wherein $R^2$ and $R^3$ are different and each represents a hydrogen atom, an optionally substituted $C_{1-4}$ alkyl group or an optionally substituted $C_{6-8}$ aryl group.

7. The process for producing an optically active allene according to claim 1, wherein $R^4$ is an acetyl group, a butyryl group or a benzoyl group.

8. A process for producing an optically active allene represented by formula (1):

$$\text{HO—} \diagdown \underset{R^4—O—\diagup}{C}=C=C\underset{R^3}{\overset{R^2}{\diagup}} \quad (1)$$

wherein $R^2$ and $R^3$ are different and each represents a hydrogen atom, an optionally substituted $C_{1-20}$ alkyl group or an optionally substituted $C_{6-20}$ aryl group, and $R^4$ represents an acyl group, which comprises reacting an allene derivative represented by formula (2):

$$\text{R}^1\text{—O—} \diagdown \underset{R^1—O—\diagup}{C}=C=C\underset{R^3}{\overset{R^2}{\diagup}} \quad (2)$$

wherein $R^1$ represents a hydrogen atom or an optionally substituted acyl group and $R^2$ and $R^3$ have the same meaning as defined above, with an acylating agent having an acyl group represented by $R^4$ when both $R^1$'s are each a hydrogen atom or with water when both $R^1$'s are each an acyl group represented by $R^4$, in the presence of a lipase enzyme which is at least one member selected from the group consisting of *Candida antarctica* lipase, *Pseudomonas fluorescens* lipase, *Pseudomonos cepacia* lipase, *Porcine liver* esterase and *Candida rugosa* lipase.

9. The process for producing an optically active allene according to claim 8, wherein the lipase enzyme is at least one member selected from the group consisting of *Candida antarctica* lipase, *Pseudomonas fluorescens* lipase and *Pseudomonas cepacia* lipase.

10. The process for producing an optically active allene according to any one of claims 8 or 9, wherein $R^4$ is an acetyl group, a butyryl group or a benzoyl group.

* * * * *